(12) United States Patent
Park et al.

(10) Patent No.: US 7,488,855 B2
(45) Date of Patent: Feb. 10, 2009

(54) METHOD OF ISOLATING 1,3-PROPANEDIOL OR 1,3-PROPANEDIOL AND 1,2-PROPANEDIOL FROM SOLUTION CONTAINING 1,3-PROPANEDIOL, 1,2-PROPANEDIOL, GLYCEROL, AND GLUCOSE

(75) Inventors: Young-Hoon Park, Seongnam (KR); Kwang-Myung Cho, Incheon (KR); Seong-Uk Kang, Yongin (KR); Jin-Hyun Kim, Daejeon (KR); Mi-Hae Cho, Chungcheongnam-do (KR)

(73) Assignee: CJ Corporation, Seoul (KR)

( * ) Notice: Subject to any disclaimer, the term of this patent is extended or adjusted under 35 U.S.C. 154(b) by 154 days.

(21) Appl. No.: 11/574,515

(22) PCT Filed: Sep. 1, 2005

(86) PCT No.: PCT/KR2005/002890

§ 371 (c)(1),
(2), (4) Date: Mar. 1, 2007

(87) PCT Pub. No.: WO2006/025697

PCT Pub. Date: Mar. 9, 2006

(65) Prior Publication Data

US 2008/0097130 A1 Apr. 24, 2008

(30) Foreign Application Priority Data

Sep. 1, 2004 (KR) ...................... 10-2004-0069565

(51) Int. Cl.
*C07C 29/68* (2006.01)
(52) U.S. Cl. ..................................................... 568/868
(58) Field of Classification Search ................. 568/868
See application file for complete search history.

(56) References Cited

U.S. PATENT DOCUMENTS

| 5,008,473 | A | 4/1991 | Breitkopf et al. |
| 5,527,973 | A | 6/1996 | Kelsey |
| 6,361,983 | B1 | 3/2002 | Ames |
| 6,428,992 | B1 | 8/2002 | Roturier et al. |
| 6,603,048 | B1 | 8/2003 | Corbin et al. |
| 2002/0133049 | A1 | 9/2002 | Hilaly et al. |

FOREIGN PATENT DOCUMENTS

| JP | 2004229660 A2 | 8/2004 |
| KR | 20020037064 A1 | 5/2002 |
| WO | 9635795 A1 | 11/1996 |
| WO | 0125178 A1 | 4/2001 |

OTHER PUBLICATIONS

Beibl et al, "Fermentation of glycerol to 1,3-propanediol: use of cosubstrates," 1995, vol. 44, pp. 15-19.

*Primary Examiner*—Elvis O Price
(74) *Attorney, Agent, or Firm*—Rothwell, Figg, Ernst & Manbeck

(57) ABSTRACT

A method of isolating 1,3-propanediol from a solution containing 1,3-propanediol, 1,2-propanediol, glycerol, and glucose is provided. The method includes: obtaining a concentrate by concentrating the solution via reduced pressure evaporation; dissolving the concentrate in a solvent selected from the group consisting of ethyl acetate, methyl ethyl ketone, and a mixture thereof and leaving the solution alone to fractionate the compounds in a solvent layer and a water layer; and loading the solvent layer in a silica-filled column under a low pressure liquid chromatography condition and eluting the solvent layer with a mixed solvent of methanol and at least one solvent which is miscible with methanol and has a polarity lower than methanol.

5 Claims, 6 Drawing Sheets

METHOD OF ISOLATING 1,3-PROPANEDIOL OR 1,3-PROPANEDIOL AND 1,2-PROPANEDIOL FROM SOLUTION CONTAINING 1,3-PROPANEDIOL, 1,2-PROPANEDIOL, GLYCEROL, AND GLUCOSE

CROSS-REFERENCE TO RELATED PATENT APPLICATION

This application is a 35 U.S.C. § 371 National Phase Entry Application from PCT/KR2005/002890, filed Sep. 1, 2005, and designating the United States.

BACKGROUND OF THE INVENTION

1. Field of the Invention

The present invention relates to a method of isolating 1,3-propanediol or 1,3-propanediol and 1,2-propanediol from a solution containing 1,3-propanediol, 1,2-propanediol, glycerol, and glucose.

2. Description of the Related Art 1,3-propanediol is also called trimethylene glycol, 1,3-dihydroxypropane or 1,3-propylene glycol and has a molecular weight of 76, a freezing point of −27° C., a boiling point of 210° C. and a viscosity of 1.053 cP. 1,3-propanediol is a light yellow, very sticky, weak acidic, water-miscible liquid. 1,3-propanediol is a primary monomer of polytrimethylene terephthalate (3GT) that is high performance polyester having various applications in clothes, carpet, etc. 1,3-propanediol is a very important intermediate in the production of polyester, polyether and polyurethane.

Many studies on isolation and purification of 1,3-propanediol have been conducted, which revealed several problems due to water-miscibility and similar properties of 1,2-propanediol and 1,3-propanediol. U.S. Pat. No. 5,008,473 discloses a method of purifying 1,3-propanediol produced by hydrolysis of acrolein by extracting the diol with cyclohexane. However, since cyclohexane has properties different from a solution containing glucose, glycerol and 1,2-propanediol, it is difficult to apply said method to isolation of 1,3-propanedipl from a fermented medium or other solutions containing glucose, glycerol and 1,2-propanediol.

U.S. Patent Application Publication No. 2002/0133049 discloses a method of recovering 1,3-propanediol from a liquid composition using a cation exchange resin. However, since 1,3-propanediol, 1,2-propanediol, glucose and glycerol do not have an ion exchange property, these cannot be isolated from one another. Thus, said method does not provide sufficiently high purity and yield of 1,3-propanediol.

U.S. Pat. No. 6,428,992 discloses a method of isolating 1,3-propanediol using a cation exchange resin whose cation is selected from the group consisting of lanthanum, lead, iron, zinc and aluminum. However, cations are materials harmful or dangerous to the human body.

Korean Patent Publication No. 2002-0037064 discloses a method of isolating 1,3-propanediol from a biological mixture using zeolite. However, there is no description regarding a specific purity of 1,3-propanediol. U.S. Pat. Nos. 5,527,973 and 6,361,983 disclose a method of isolating 1,3-propanediol using distillation. However, distillation requires high energy and is inefficient in the removal of 1,2-propanediol having a boiling point of 187.6° C.

Therefore, there is a still demand for a method of efficiently isolating 1,3-propandiol with a high purity from a biological culture medium or other solutions containing glucose, glycerol and 1,2-propanediol.

SUMMARY OF THE INVENTION

The present invention provides a method of efficiently isolating 1,3-propanediol from a solution containing 1,3-propanediol, 1,2-propanediol, glycerol, and glucose.

The present invention also provides a method of efficiently isolating 1,3-propanediol and 1,2-propanediol from a solution containing 1,3-propanediol, 1,2-propanediol, glycerol, and glucose.

According to an aspect of the present invention, there is provided a method of isolating 1,3-propanediol from a solution containing 1,3-propanediol, 1,2-propanediol, glycerol, and glucose, the method comprising:

obtaining a concentrate by concentrating the solution via reduced pressure evaporation;

dissolving the concentrate in a solvent selected from the group consisting of ethyl acetate, methyl ethyl ketone, and a mixture thereof and leaving the solution alone to fractionate the compounds in a solvent layer and a water layer; and loading the solvent layer in a silica-filled column under a low pressure liquid chromatography condition and eluting the solvent layer with a mixed solvent of methanol and at least one solvent which is miscible with methanol and has a polarity lower than methanol.

According to another aspect of the present invention, there is provided a method of isolating 1,3-propanediol and 1,2-propanediol from a solution containing 1,3-propanediol, 1,2-propanediol, glycerol, and glucose, the method comprising:

obtaining a concentrate by concentrating the solution via reduced pressure evaporation; and dissolving the concentrate in a solvent selected from the group consisting of ethyl acetate, methyl ethyl ketone, and a mixture thereof and leaving the solution alone to fractionate the compounds in a solvent layer and a water layer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
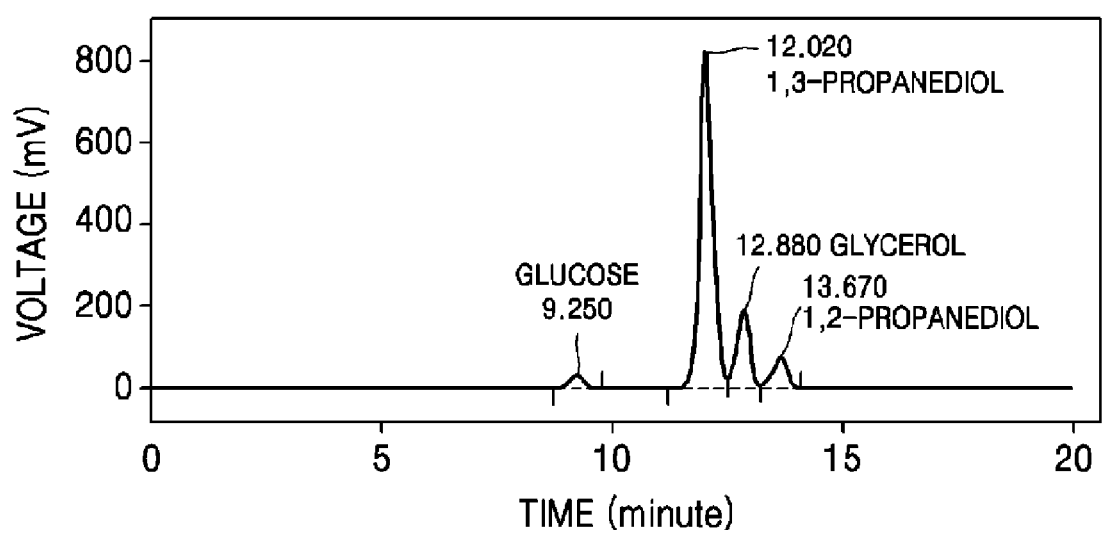
FIG. 1 is a HPLC analysis result of a solution containing 1,3-propanediol, 1,2-propanediol, glucose and glycerol.
Figure 2A:
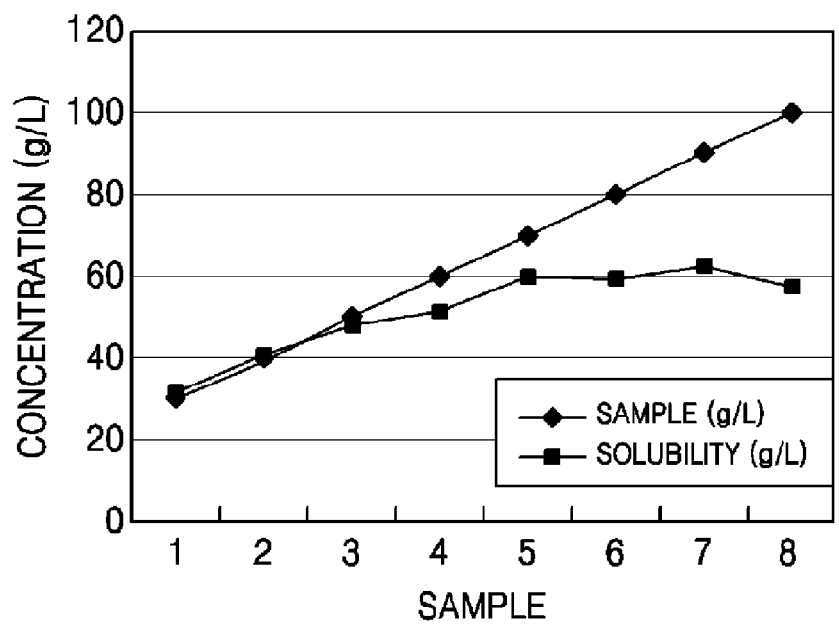
FIGS. 2A through 2D are graphs illustrating the solubility of each of 1,3-propanediol, 1,2-propanediol, glycerol, and glucose in ethyl acetate (EA)
Figure 2B:
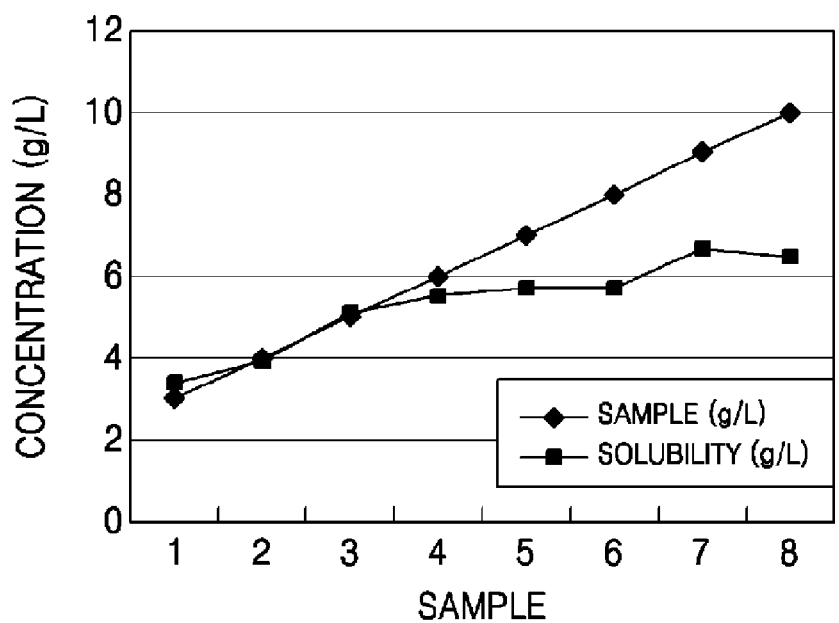
Figure 2C:
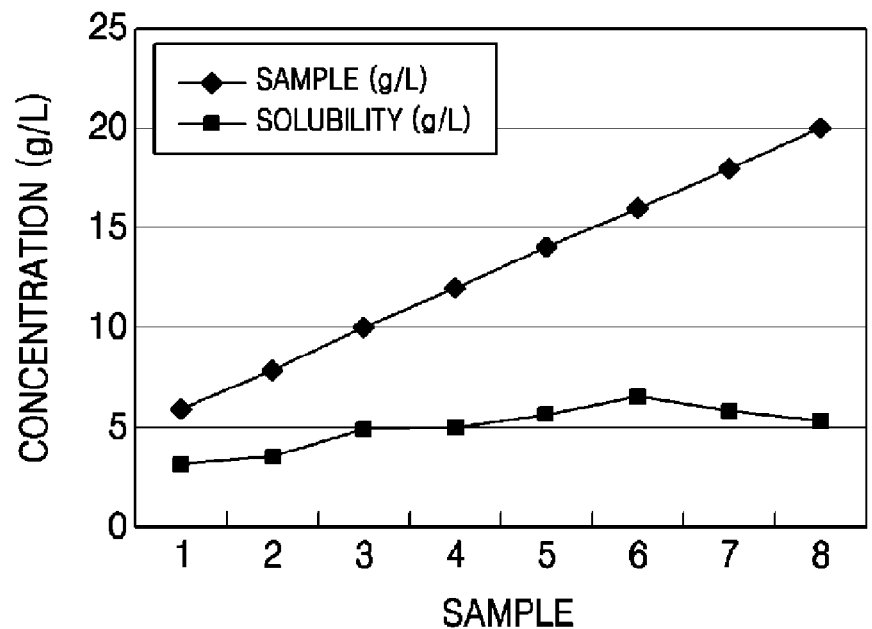
Figure 2D:
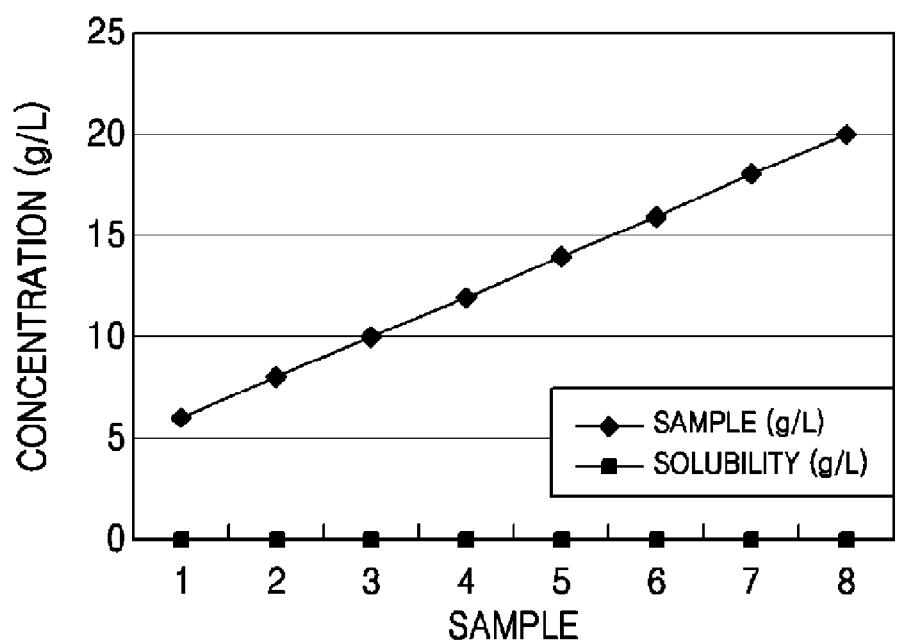

A method of isolating 1,3-propanediol from a solution containing 1,3-propanediol, 1,2-propanediol, glycerol, and glucose according to an embodiment of the present invention includes: obtaining a concentrate by concentrating the solution via reduced pressure evaporation; dissolving the concentrate in a solvent selected from the group consisting of ethyl acetate, methyl ethyl ketone, and a mixture thereof and leaving the solution alone to fractionate the compounds in a solvent layer and a water layer; and loading the solvent layer in a silica-filled column under a low pressure liquid chromatography condition and eluting the solvent layer with a mixed solvent of methanol and at least one solvent which is miscible with methanol and has a polarity lower than methanol.

In the method, a solution containing 1,3-propanediol, 1,2-propanediol, glycerol, and glucose is concentrated by reduced pressure evaporation to remove water. Next, the obtained concentrate is dissolved in a solvent selected from the group consisting of ethyl acetate, methyl ethyl ketone, and a mixture thereof and left alone to fractionate the compounds in a solvent layer and a water layer. In an embodiment of the method, the amount of the concentrate dissolved in the solvent is such that the concentration of 1,3-propanediol in the solvent is 5-100 g/L, preferably 35-45 g/L. Due to the fractionation, 1,3-propanediol, 1,2-propanediol, glycerol, and glucose in the solution are distributed in the solvent layer and the water layer according to their solubility in the solvent and water. Most of 1,3-propanediol and 1,2-propanediol is distributed in the solvent layer and glucose and a part of glycerol are distributed in the water layer. Thus, by taking the solvent layer, 1,3-propanediol and 1,2-propanediol containing no glucose and a part of glycerol can be first isolated from the solution.

The obtained solvent layer is loaded in a silica-filled column under a low pressure liquid chromatography condition and is eluted with a mixed solvent of methanol and at least one solvent which is miscible with methanol and has a polarity lower than methanol to finally isolate 1,3-propanediol from the solution containing 1,3-propanediol, 1,2-propanediol, glycerol, and glucose. Herein, the low pressure liquid chromatography takes place at a relatively low pressure, for example, at about 120 psi or less, in contrast to a high pressure liquid chromatography (HPLC). The solvent miscible with methanol and having a polarity lower than methanol may be selected from the group consisting of ethyl acetate, methyl ethyl ketone, and a mixture thereof. Methanol and at least one solvent selected from the group consisting of ethyl acetate, methyl ethyl ketone, and a mixture thereof may be mixed in a ratio of 90:10 to 99.9:0.9, preferably 97:3 to 99:1.

A method of isolating 1,3-propanediol and 1,2-propanediol from a solution containing 1,3-propanediol, 1,2-propanediol, glycerol, and glucose according to another embodiment of the present invention includes: obtaining a concentrate by concentrating the solution via reduced pressure evaporation; and dissolving the concentrate in a solvent selected from the group consisting of ethyl acetate, methyl ethyl ketone, and a mixture thereof and leaving the solution alone to fractionate the compounds in a solvent layer and a water layer.

In the method, a solution containing 1,3-propanediol, 1,2-propanediol, glycerol, and glucose is concentrated by reduced pressure evaporation to remove water. Next, the obtained concentrate is dissolved in a solvent selected from the group consisting of ethyl acetate, methyl ethyl ketone, and a mixture thereof and left alone to fractionate the compounds in a solvent layer and a water layer. In an embodiment of the method, the amount of the concentrate dissolved in the solvent is such that the concentration of 1,3-propanediol in the solvent is 5-100 g/L, preferably 35-45 g/L. By the fractionation, 1,3-propanediol, 1,2-propanediol, glycerol, and glucose in the solution are distributed in the solvent layer and the water layer according to their solubility in the solvent and water. Most of 1,3-propanediol and 1,2-propanediol is distributed in the solvent layer and glucose and a part of glycerol are distributed in the water layer. Thus, by taking the solvent layer, 1,3-propanediol and 1,2-propanediol containing no glucose and a part of glycerol can be isolated from the solution.

The present invention will now be described in greater detail with reference to the following examples. The following examples are for illustrative purposes only and are not intended to limit the scope of the invention.

EXAMPLES

Example 1

Removal of Water from Solution by Reduced Pressure Evaporation

A solution containing 1,3-propanediol, 1,2-propanediol, glycerol, and glucose (10:1:2:2) was evaporated under reduced pressure at a temperature of 80° C. or higher to remove water, thereby obtaining a concentrate.

The obtained concentrate was completely dried and dissolved in water. Then, the solution was analysed through HPLC under the conditions given in Table 1. The HPLC results were given in Table 1.

TABLE 1

| | |
|---|---|
| Apparatus | HPLC (Waters) |
| Column | ID 6.5 mm × L 300 mm |
| Filler | Sugar-Pak (Waters) |
| Column temperature | 90° C. |
| Mobile phase | Distilled water |
| Flow rate | 0.5 mL/min |
| Injection volume | 20 µl |
| Solvent | Distilled water |

Example 2

Partial Removal of Glucose and Glycerol by Fractionation Using Ethyl Acetate (EA) and Phase Separation To establish an optimum phase separation condition using EA, a solution containing 1,3-propanediol, 1,2-propanediol, glycerol, and glucose (10:1:2:2) was dissolved in EA such that the concentration of 1,3-propanediol in EA was 30-100 g/L. Then, the solution was left alone for 2 hours. An upper solvent layer was separated and components therein were analysed through HPLC under the conditions given in Table 1. The results were illustrated in FIGS. 2A through 2D. FIGS. 2A through 2D are graphs illustrating the solubility of each of 1,3-propanediol, 1,2-propanediol, glycerol, and glucose in EA. Referring to FIGS. 2A through 2D, the solubility of 1,3-propanediol was about 40 g/L and solubilities of 1,2-propanediol and glycerol were 5-7 g/L and 3-6 g/L, respectively.

It was identified from the experimental results that by using ethyl acetate, glucose can be removed from the solution containing 1,3-propanediol, 1,2-propanediol, glycerol, and glucose.

Example 3

Partial Removal of Glucose and Glycerol by Fractionation Using Methyl Ethyl Ketone and Phase Separation The experiment was carried out in the same manner as in Example 2, except that methyl ethyl ketone was used as a solvent. As a result, it can be seen that solubilities of 1,3-propanediol, 1,2-propanediol, glycerol, and glucose in methyl ethyl ketone are similar to solubilities thereof in EA (data was not shown).

It was identified from the experimental results that by using methyl ethyl ketone, glucose can be removed from the solution containing 1,3-propanediol, 1,2-propanediol, glycerol, and glucose.

Example 4

Purification of 1,3-propanediol from Solvent Layer Containing 1,3-propanediol Through Low Pressure Liquid Chromatography on Silica A silica resin (size 0.040-0.063 mm, MERCK) was filled in a column with a diameter of 2 cm and a length of 180 cm and was stabilized using a 98:2 mixture of EA and methanol (MeOH) as a mobile phase. Next, a solution containing 1,3-propanediol, 1,2-propanediol, glycerol, and glucose (10:1:2:2) in EA was prepared such that the concentration of 1,3-propanediol in EA was 40 g/L. Then, the solution was loaded in the column in sample volumes of 40 mL, 60 mL and 20 mL.

Figure 3:
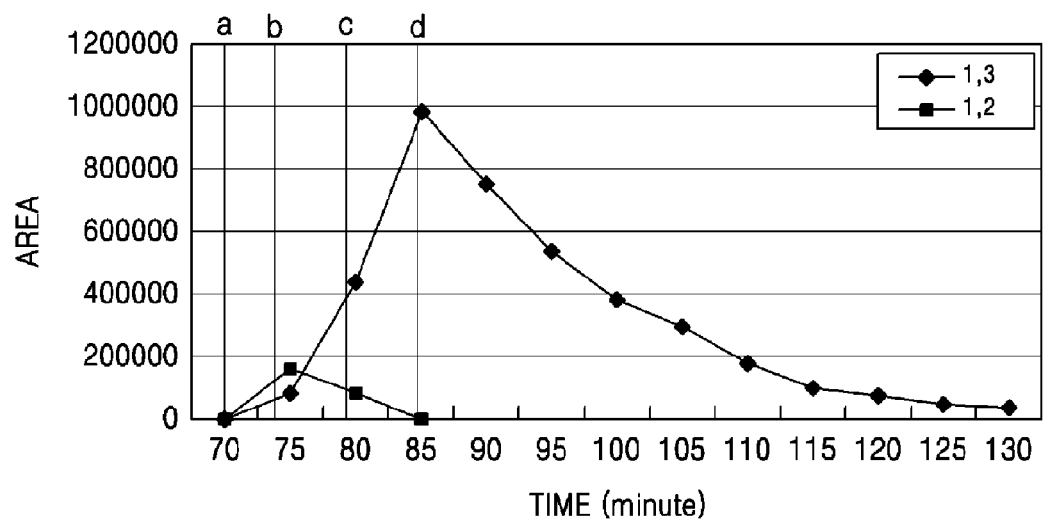
FIGS. 3 through 5 are chromatograms of 40 mL, 60 mL and 20 mL of a solution containing 1,3-propanediol, 1,2-propanediol, glycerol, and glucose (10:1:2:2) in EA (the concentration of 1,3-propanediol in EA: 40 g/L)
Figure 4:
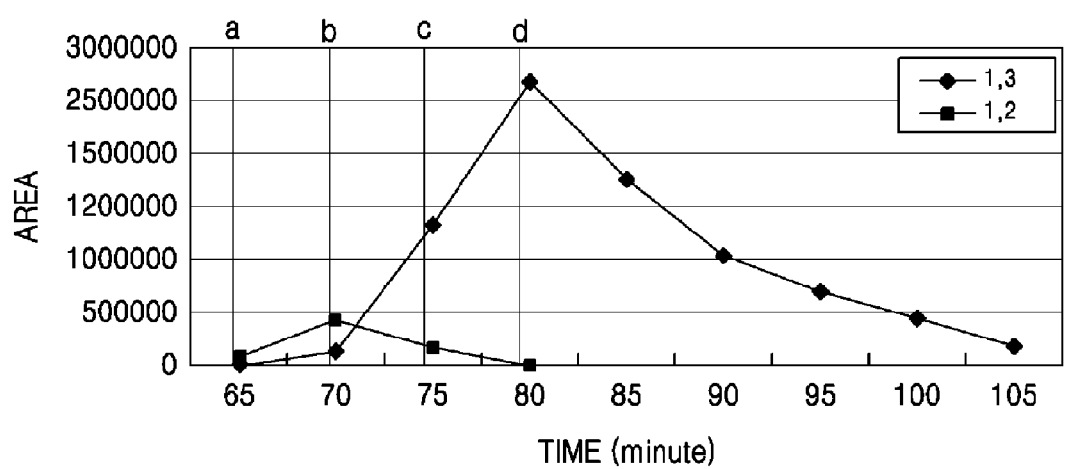
Figure 5:
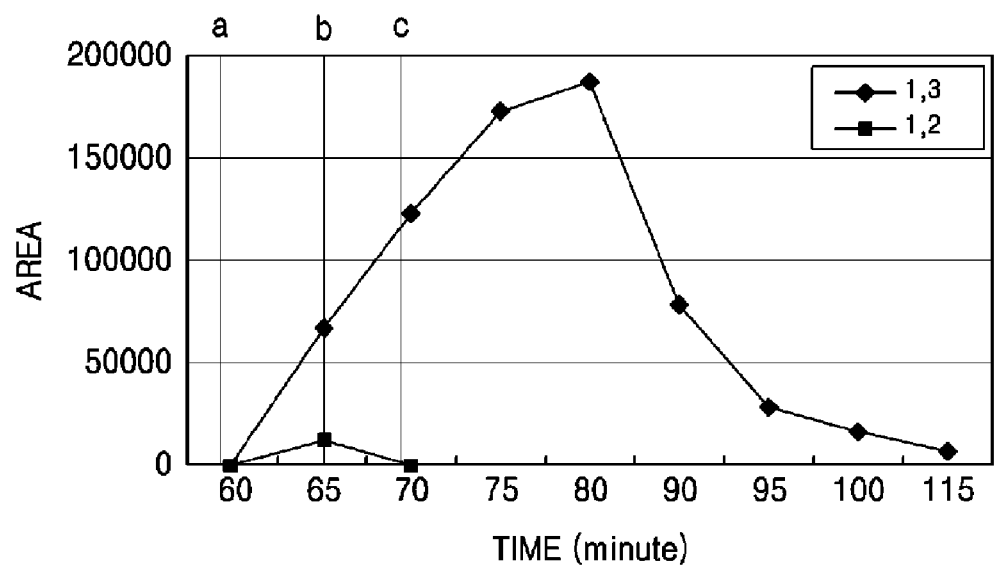

The 98:2 mixture of EA and MeOH was applied to the column at a flow rate of 10 mL/min and fractions of 50 mL were obtained at intervals of 5 minutes. The fractions were concentrated and dried, and then dissolved in distilled water. The solution was analysed through HPLC under the conditions given in Table 1. The results were illustrated in FIGS. 3 through 5. FIGS. 3 through 5 are chromatograms of 40 mL, 60 mL and 20 mL of the solution containing 1,3-propanediol, 1,2-propanediol, glycerol, and glucose (10:1:2:2). In FIG. 3, $a, b, c,$ and $d$ respectively designate points at 70, 75, 80 and 85 minutes after starting elution. When fractions were recovered after these points, the yield and purity of 1,3-propanediol were 96% and 94%, 92% and 95%, 82% and 98%, and 64% and 100%, respectively. In FIG. 4, $a, b, c,$ and $d$ respectively designate points at 65, 70, 75 and 80 minutes after starting elution. When fractions were recovered after these points, the yield and purity of 1,3-propanediol were 81% and 91%, 78% and 94%, 66% and 98%, and 42% and 100%, respectively. In FIG. 5, $a, b,$ and $c$ respectively designate points of 60, 65 and 70 minutes after starting elution. When fractions were recovered after these points, the yield and purity of 1,3-propanediol were 68% and 93%, 60% and 98%, and 50% and 100%, respectively.

Example 5

Purification of 1,3-propanediol from Solvent Layer Containing 1,3-propanediol Through Low Pressure Liquid Chromatography on Silica A silica resin (size 0.040-0.063 mm, MERCK) was filled in a column with a diameter of 2 cm and a length of 180 cm and was stabilized using a 98:2 mixture of methyl ethyl ketone (MEK) and methanol (MeOH) as a mobile phase. Next, a solution containing 1,3-propanediol, 1,2-propanediol, glycerol, and glucose (10:1:2:2) in MEK was prepared such that the concentration of 1,3-propanediol in MEK was 40 g/L. Then, the solution was loaded in the column in sample volumes of 40 mL, 60 mL and 80 mL.

Figure 6:
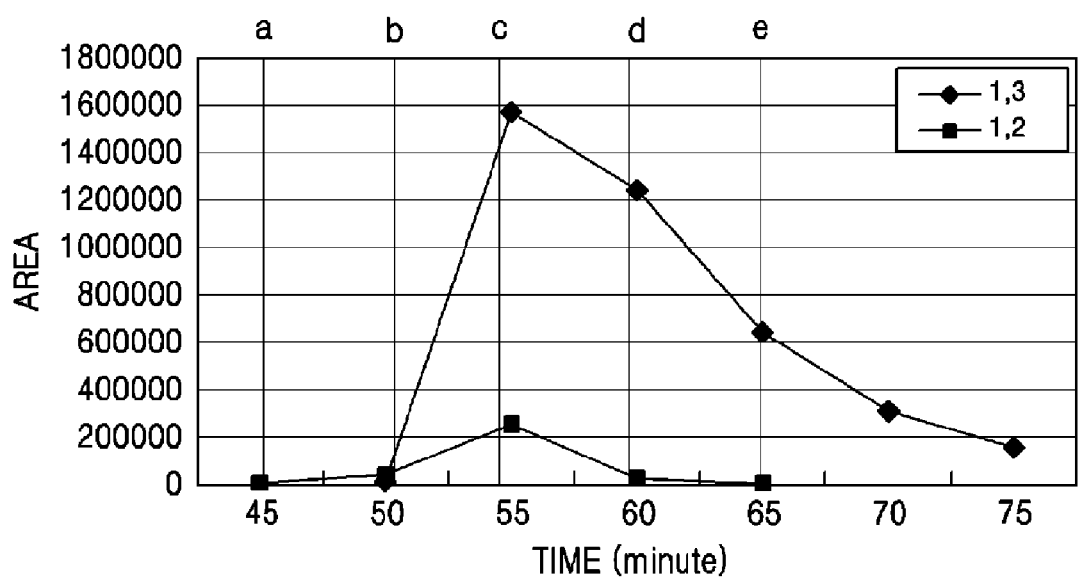
FIGS. 6 through 8 are chromatograms of 40 mL, 60 mL and 80 mL of a solution containing 1,3-propanediol, 1,2-propanediol, glycerol, and glucose (10:1:2:2) in methyl ethyl ketone (MEK) (the concentration of 1,3-propanediol in MEK: 40 g/L).
Figure 7:
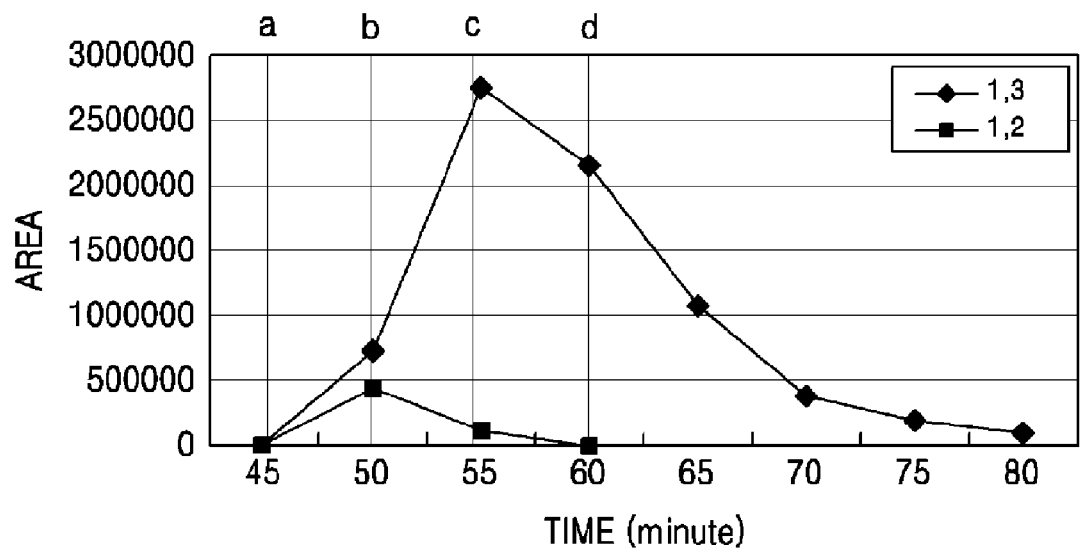
Figure 8:
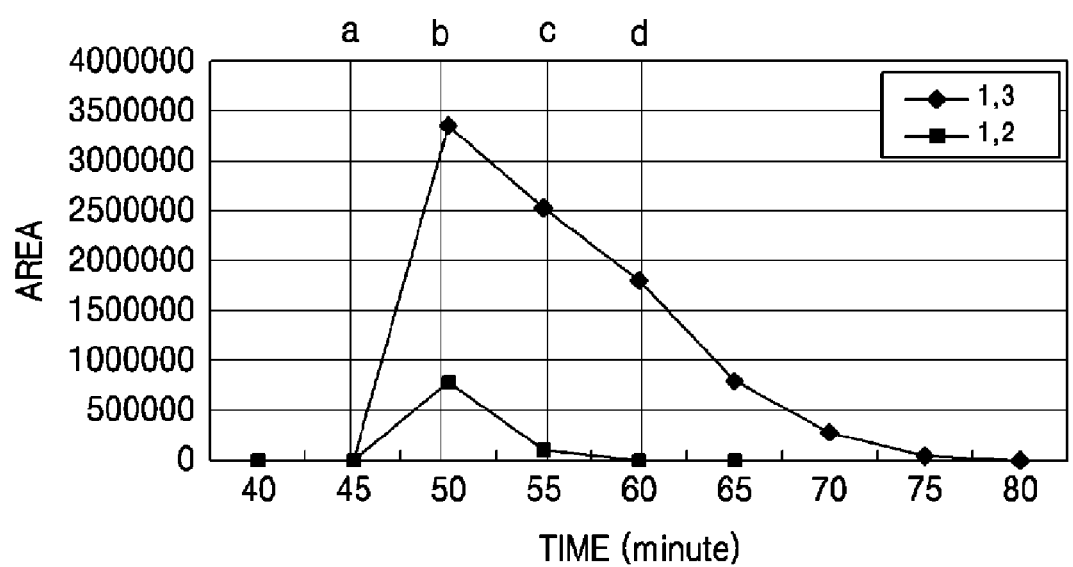

The 98:2 mixture of MEK and MeOH was applied to the column at a flow rate of 10 mL/min and fractions of 50 mL were obtained at intervals of 5 minutes. The fractions were concentrated and dried, and then dissolved in distilled water. The solution was analysed through HPLC under the conditions given in Table 1. The results were illustrated in FIGS. 6 through 8. FIGS. 6 through 8 are chromatograms of 40 mL, 60 mL and 80 mL of the solution containing 1,3-propanediol, 1,2-propanediol, glycerol, and glucose (10:1:2:2). In FIG. 6, $a, b, c, D,$ and $e$ respectively designate points at 45, 50, 55, 60 and 65 minutes after starting elution. When fractions were recovered after these points, the yield and purity of 1,3-propanediol were 79% and 94%, 76% and 95%, 48% and 96%, 26% and 98%, and 13% and 100%, respectively. In FIG. 7, $a, b, c,$ and $d$ respectively designate points at 45, 50, 55 and 60 minutes after starting elution. When fractions were recovered after these points, the yield and purity of 1,3-propanediol were 91% and 91%, 81% and 92%, 51% and 98%, and 26% and 100%, respectively. In FIG. 8, $a, b, c,$ and $d$ respectively designate points at 45, 50, 55 and 60 minutes after starting elution. When fractions were recovered after these points, the yield and purity of 1,3-propanediol were 80% and 91%, 78% and 92%, 50% and 98%, and 29% and 100%, respectively.

According to the method of isolating 1,3-propanediol of the present invention, 1,3-propanediol can be efficiently isolated from a solution containing 1,3-propanediol, 1,2-propanediol, glycerol, and glucose.

According to the method of isolating 1,3-propanediol and 1,2-propanediol of the present invention, 1,3-propanediol and 1,2-propanediol containing no glucose and a part of glycerol can be efficiently isolated from a solution containing 1,3-propanediol, 1,2-propanediol, glycerol, and glucose.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of isolating 1,3-propanediol from a solution containing 1,3-propanediol, 1,2-propanediol, glycerol, and glucose, the method comprising:
    obtaining a concentrate by concentrating the solution via reduced pressure evaporation;
    dissolving the concentrate in a solvent selected from the group consisting of ethyl acetate, methyl ethyl ketone, and a mixture thereof and leaving the solution alone to fractionate the compounds in a solvent layer and a water layer; and
    loading the solvent layer in a silica-filled column under a low pressure liquid chromatography condition and eluting the solvent layer with a mixed solvent of methanol and at least one solvent which is miscible with methanol and has a polarity lower than methanol.

2. The method of claim 1, wherein the solvent which is miscible with methanol and has a polarity lower than methanol is selected from the group consisting of ethyl acetate, methyl ethyl ketone, and a mixture thereof.

3. The method of claim 1, wherein methanol and at least one solvent selected from the group consisting of ethyl acetate, methyl ethyl ketone, and a mixture thereof are mixed in a ratio of 90:10 to 99.9:0.9.

4. A method of isolating 1,3-propanediol and 1,2-propanediol from a solution containing 1,3-propanediol, 1,2-propanediol, glycerol, and glucose, the method comprising:
    obtaining a concentrate by concentrating the solution via reduced pressure evaporation; and
    dissolving the concentrate in a solvent selected from the group consisting of ethyl acetate, methyl ethyl ketone, and a mixture thereof and leaving the solution alone to fractionate the compounds in a solvent layer and a water layer.

5. The method of claim 1, wherein the concentrate is dissolved in the solvent such that the concentration of 1,3-propanediol in the solvent is 35-45 g/L.

* * * * *